United States Patent
Ikari et al.

[19]

[11] Patent Number: 5,876,385
[45] Date of Patent: Mar. 2, 1999

[54] CATHETER

[75] Inventors: Yuuji Ikari; Naofumi Okajima, both of Tokyo, Japan

[73] Assignee: Terumo Kabushiki Kaisha, Tokyo, Japan

[21] Appl. No.: 927,486

[22] Filed: Sep. 11, 1997

[30] Foreign Application Priority Data

Sep. 13, 1996 [JP] Japan .................................. 8-242789

[51] Int. Cl.⁶ .................................................. A61M 25/00
[52] U.S. Cl. ............................................ 604/280; 604/281
[58] Field of Search .................................. 604/264, 280, 604/281, 282; 138/177, 178

[56] References Cited

U.S. PATENT DOCUMENTS

| 4,898,591 | 2/1990 | Jang et al. ............................... 604/264 |
| 5,401,258 | 3/1995 | Voda . |
| 5,476,453 | 12/1995 | Mehta . |

FOREIGN PATENT DOCUMENTS 0 277 366   8/1988   European Pat. Off. .
0 728 494   8/1996   European Pat. Off. .
93/21983   11/1993   WIPO .

*Primary Examiner*—John D. Yasko
*Attorney, Agent, or Firm*—Burns, Doane, Swecker & Mathis, LLP

[57] ABSTRACT

A catheter is provided whose distal end can be introduced through an artery in the arm into the entrance of the left coronary artery. The catheter includes a catheter body having an outer diameter of at most 2.7 mm over its entire length and has a proximal segment straight under a free state and a distal segment having a curved shape under a free state. The distal segment includes a first straight portion contiguous to the proximal segment through a first curved portion, a second straight portion contiguous to the first straight portion through a second curved portion bent in a direction opposite to the bending direction of the first curved portion, a third straight portion contiguous to the second straight portion through a third curved portion bent in the bending direction of the second curved portion, and a straight distal end portion contiguous to the third straight portion through a fourth curved portion bent in the bending direction of the third curved portion.

20 Claims, 3 Drawing Sheets

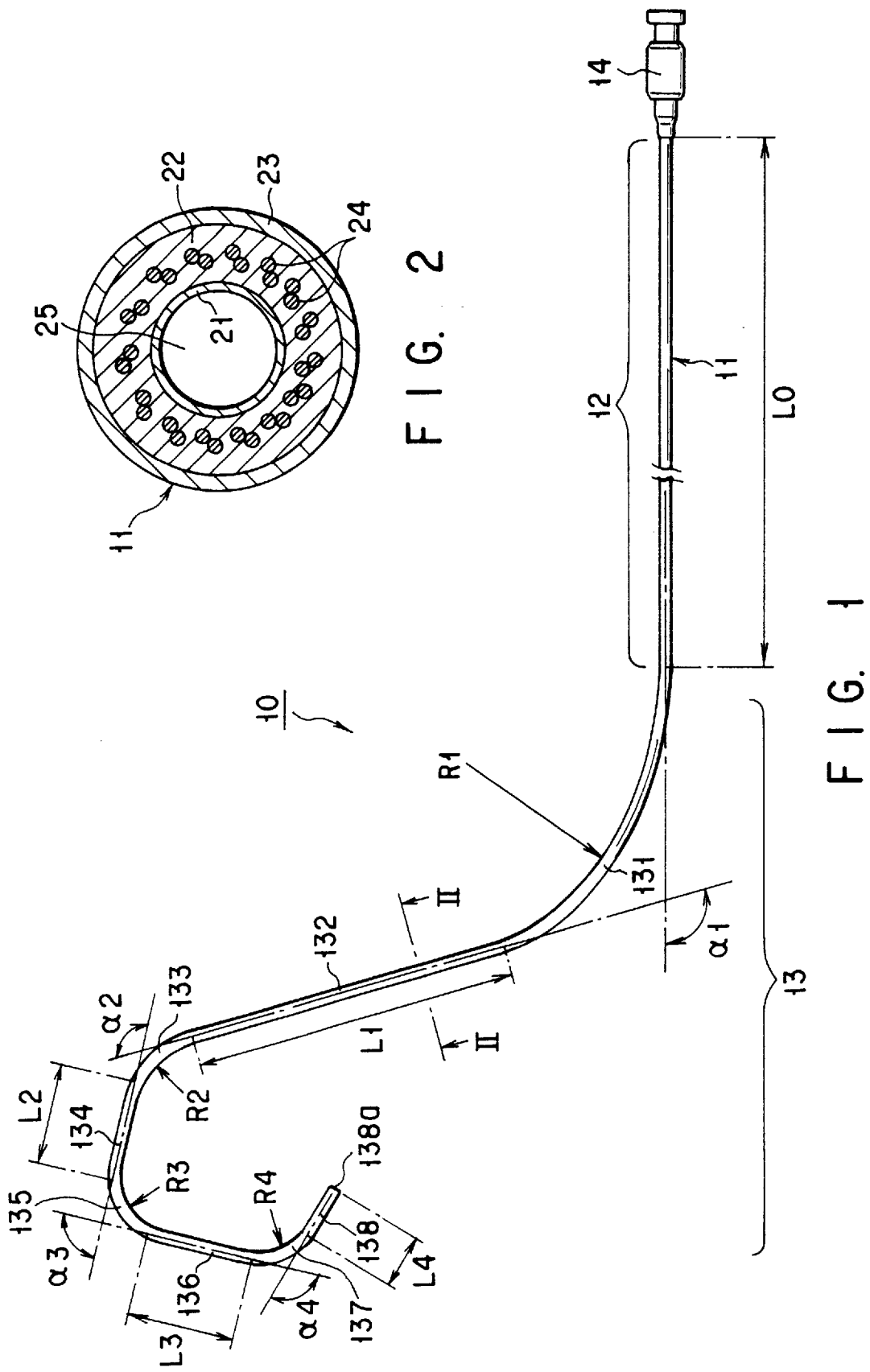

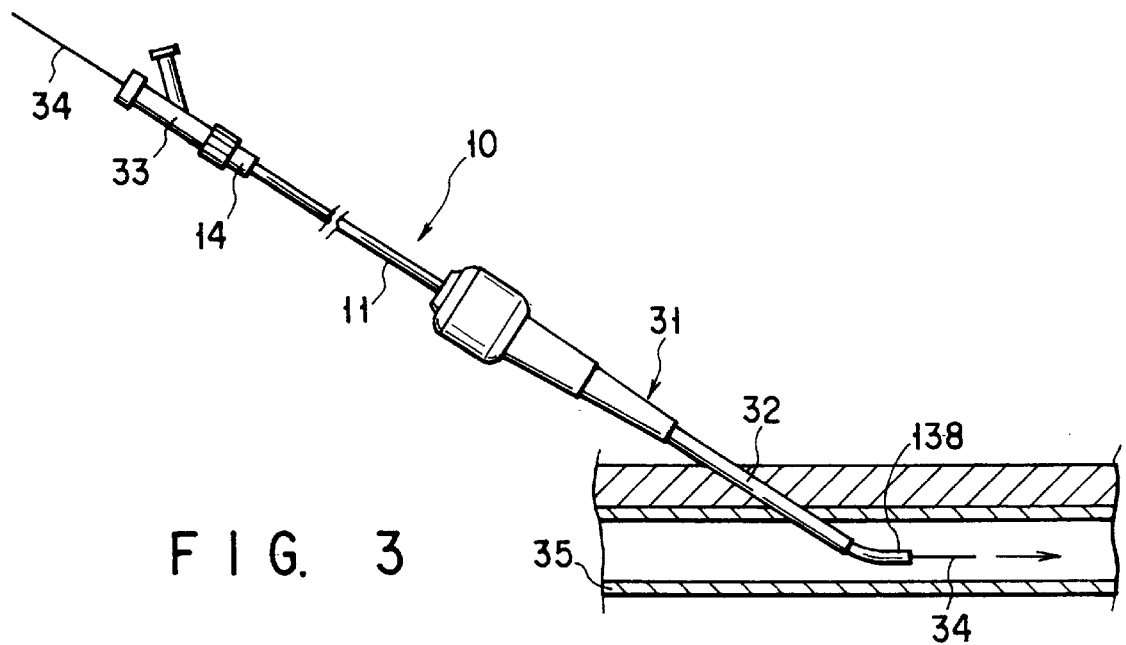
F I G. 3
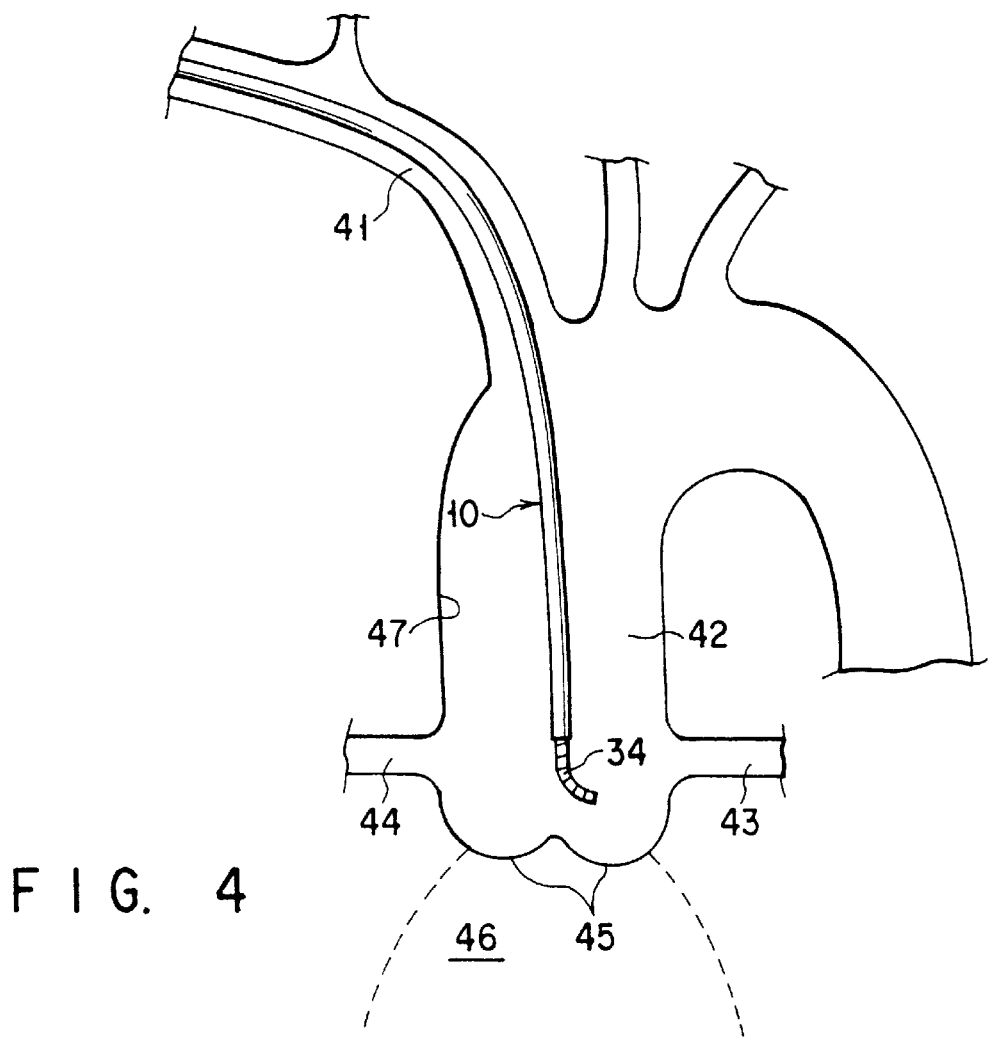
F I G. 4

CATHETER

BACKGROUND OF THE INVENTION

The present invention relates to a catheter used for angiocardiography and curing the heart or its peripheral tissues, particularly, to a catheter for coronary arteries.

Known catheters for coronary arteriography include Judkins type, Anplatzs type, etc. In general, these catheters are pierced from a femoral artery by Seldinger technique or sheath technique for selective coronary arteriography.

Treatment using a catheter is also widely employed nowadays including, for example, percutaneous transluminal coronary angioplasty (PTCA) using a balloon-tip catheter for the treatment of ischemic heart diseases. For inserting a treating catheter efficiently and with safety into a desired blood vessel, the performance of the treating catheter is very important. For example, it is necessary to use together a guiding catheter which permits alleviating the reaction brought about by the insertion of the treating catheter and also permits imparting a sufficient back-up force to the treating catheter so as to provide an effective assistance for smooth insertion of the treating catheter. Like the catheter for coronary arteriography, the known guiding catheters also include Judkins type, Anplatzs type, etc. In general, the guiding catheter is inserted from the femoral artery by Seldinger technique or sheath technique to selectively secure the coronary arteries, followed by inserting a treating catheter such as a balloon-catheter for PTCA within the guiding catheter.

In the conventional angiography or treatment using a catheter, a femoral region is pierced by the catheter and hemostasis is applied to the piercing portion after the operation. Therefore, the patient is required to lie absolutely quiet, leading to a serious problem. For example, it is necessary for the patient to urinate, evacuate, and take food and drink while lying on his back so as to give considerable pains such as pains in the waist portion to the patient. Further, where the catheter is pierced from the femoral region, bleeding is likely to take place even if the patient keeps quiet. If the bleeding reaches the cavitas peritonealis, the patient's life is endangered. Still further, urination while lying on the back is made difficult in some cases. A urinary tract catheter is used in this case. However, use of the particular catheter tends to bring about a urinary tract infectious disease.

For eliminating or suppressing these problems, it is considered effective to pierce a catheter from an artery in the arm, particularly, a brachial artery, or a radial artery. If the catheter is pierced from an artery in the arm, the patient is able to walk immediately after the operation by simply keeping the piercing portion in the upper arm portion stretched. Also, the patient is free from pains in the waist portion and able to urinate, evacuate and take food and drink as usual. Further, the urinary tract infectious disease in the cavitas peritonealis need not be worried about.

However, the catheter should originally be designed to have a shape adapted for the piercing portion. Since the catheter generally used nowadays is designed to be introduced from the femoral artery, a catheter adapted for introduction from an artery in the arm promptly and with safety is unknown to the art. Suppose the catheter for introduction from the femoral artery is used as it is for introduction from the brachial artery. In this case, the catheter introduction is made difficult and troublesome, making it necessary to perform the introducing operation repeatedly. Naturally, the operating time is increased so as to increase the burden given to the patient. Further, since the back-up force is insufficient, the distal end of the catheter fails to be introduced into the entrance of the coronary artery during the imaging operation or when the treating catheter is moved toward the peripheral sites. It follows that a sufficient angiography cannot be performed, or operation of the treating catheter is made difficult.

Under the circumstances, it is strongly required to develop a catheter of a shape adapted for introduction from the arm of the patient.

BRIEF SUMMARY OF THE INVENTION

An object of the present invention is to provide a catheter which can be introduced into the entrance of a coronary artery from an artery in the arm, e.g., a brachial artery, or a radial artery, without passing through a femoral artery so as to achieve introduction easily, with safety, and promptly and, thus, to lessen the burden of the patient after the operation.

Another object is to provide a catheter which can be used as a guiding catheter effective for ensuring the assistance of the treating catheter.

These and other objects which may be apparent from the description which follows have been achieved according to the present invention by a catheter whose distal end can be introduced via an artery in the arm into the entrance of the left coronary artery, comprising a catheter body having an outer diameter of at most 2.7 mm throughout its entire length and including a proximal segment substantially straight under a free state and a distal segment having a curved shape under a free state, the distal segment including a first substantially straight portion contiguous to the proximal segment through a first curved portion, a second substantially straight portion contiguous to the first substantially straight portion through a second curved portion bent in a direction opposite to the bending direction of the first curved portion, a third substantially straight portion contiguous to the second substantially straight portion through a third curved portion bent in the bending direction of the second curved portion, and a substantially straight distal end portion including the distal end and contiguous to the third substantially straight portion through a fourth curved portion bent in the bending direction of the third curved portion.

It is desirable for the second substantially straight portion to be shaped to permit the second substantially straight portion to be in contact with the wall of the aortic arch on the side opposite to the entrance of the left coronary artery.

It is also desirable for the first curved portion to be shaped such that, when the distal end of the catheter is positioned in the entrance of the left coronary artery, the first curved portion is located in a region from the brachiocephalic trunk to the aortic arch.

In the present invention, it is desirable for the catheter body to be formed of a laminate structure comprising a plurality of layers. It is also desirable for a reinforcing material, preferably a metal mesh, to be buried in the catheter body.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a plan view showing a catheter according to one embodiment of the present invention;

FIG. 2 is a cross sectional view along line II—II shown in FIG. 1;

FIG. 3 shows how the catheter of the present invention is introduced into a blood vessel;

FIG. 4 schematically shows the catheter of the present invention guided by a guide wire so as to be introduced into the aorta ascendens.

DETAILED DESCRIPTION OF THE INVENTION

Figure 5:
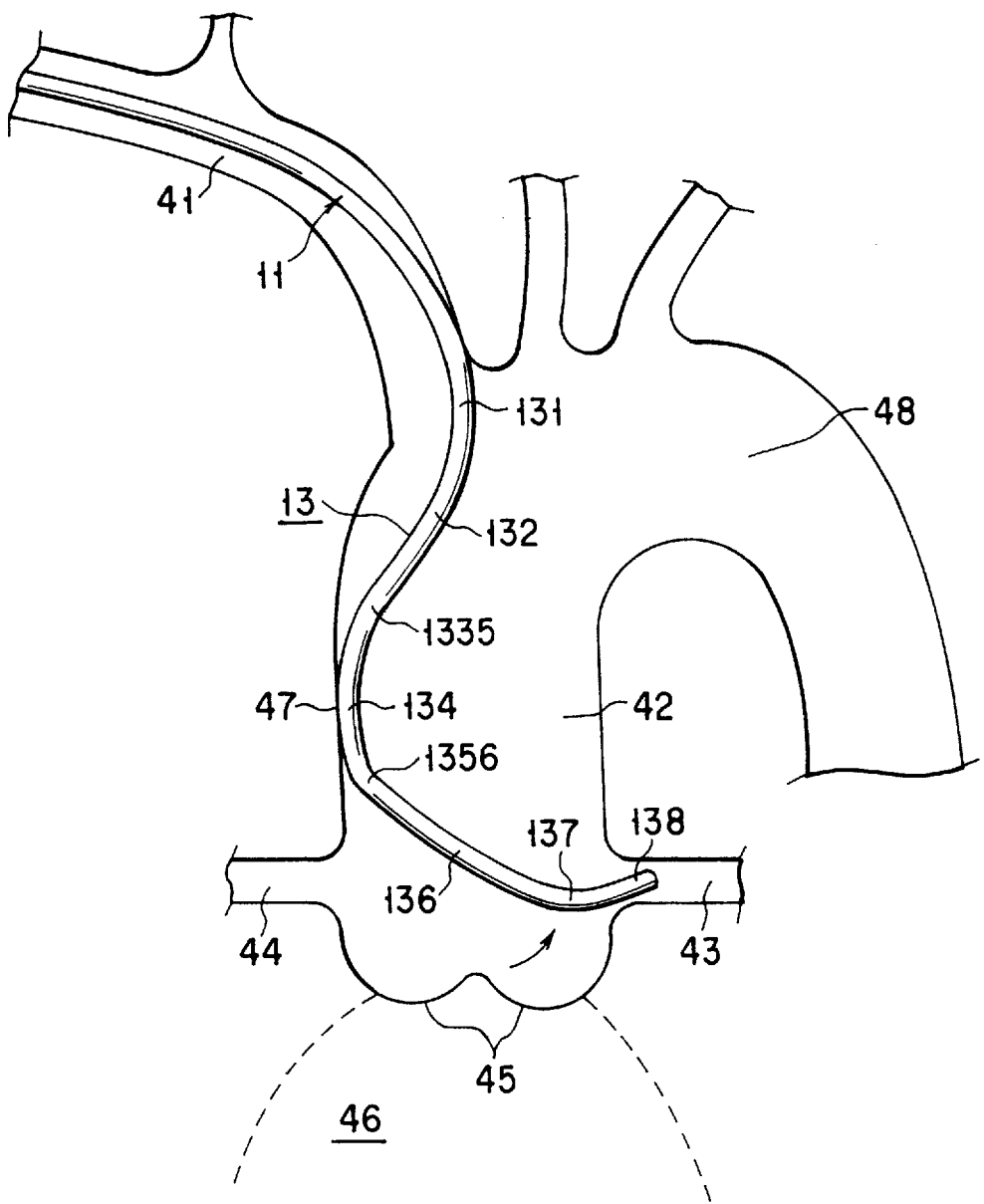
FIG. 5 schematically shows the catheter of the present invention, which is guided by a guide wire into the aorta ascendens and, then, the guide wire is withdrawn to permit the distal end of the catheter to be inserted into the entrance of the left coronary artery.

Now, a catheter according to one embodiment of the present invention will be described in detail with reference to the accompanying drawings. As shown in FIG. 1, a catheter 10 includes a catheter body 11 made of a flexible cylindrical tube. The proximal end portion of the catheter body 10 is connected to a hub 14 used for injecting a contrast medium or the like.

The catheter body 11 has an outer diameter of at most 2.7 mm, preferably at most 2.1 mm throughout its length. It is desirable to insert the catheter into a blood vessel through the brachial artery, preferably radial artery, by using a sheath in order to lessen the burden given to the patient. For inserting the catheter through the brachial artery, the outer diameter of the catheter must be made as small as possible. In general, the operability of the catheter is impaired with decrease in the outer diameter, making it difficult to select the entrance of the coronary artery. Also, for selecting the entrance of the coronary artery, the proximal end portion is rotated in many cases in the conventional catheter so as to rotate the distal end. Naturally, the catheter is required to be capable of sufficiently transmitting the torque. If the outer diameter is unduly small, however, the catheter is rendered incapable of sufficiently transmitting the torque. Also, the mechanical strength of the catheter is rendered insufficient, giving rise to occurrence of kink, twisting, etc. during operation of the catheter. Such being the situation, it was unavoidable to use mainly a thick catheter conventionally.

On the other hand, the catheter 10 of the present invention is shaped not to require capability of transmitting torque substantially, making it possible to decrease the outer diameter of the catheter so as to suppress bleeding and lessen the burden given to the patient. In general, the catheter body 11 has an outer diameter of at least 1.0 mm, preferably at least 1.5 mm.

The catheter body 11 consists of a proximal segment 12 which is substantially straight under a free state, i.e., free from external force, and a distal segment 13 having a curved shape under a free state, i.e., free from external force.

It is desirable for the proximal segment 12, which is substantially straight under a free state, to have a length L0 of 400 to 1,000 mm.

On the other hand, the distal segment 13 includes a first substantially straight portion 132 contiguous to the proximal segment 12 through a first curved portion 131, a second substantially straight portion 134 contiguous to the first substantially straight portion 132 through a second curved portion 133 bent in a direction opposite to the bending direction of the first curved portion 131, a third substantially straight portion 136 contiguous to the second substantially straight portion 134 through a third curved portion 135 bent in the bending direction of the second curved portion 133, and a distal end portion 138 contiguous to the third substantially straight portion 136 through a fourth curved portion 137 bent in the bending direction of the third curved portion 135.

The first curved portion 131 is bent under a free state (bent from the proximal segment 12 in the clockwise direction in FIG. 1). In the present invention, it is desirable for an angle α1 made in the first curved portion 131 between the proximal segment 12 and the first straight portion 132 to fall within a range of between 90° and 150° under a free state, i.e., free from external force. If the angle α1 exceeds 150°, the catheter body 11 tends to unduly expand the junction between the subclavian artery and the brachiocephalic trunk so as to give pains to the patient. If the angle α1 is smaller than 90°, however, it is difficult for the distal end 138a of the catheter body 11 to be inserted into the entrance of the left coronary artery. Even if inserted, it is difficult to obtain a sufficient back-up force. Where the angle α1 falls within the range noted above, a sufficient repulsive force is generated when a guide wire is withdrawn from the catheter inserted from the brachiocephalic trunk into the aorta ascendens to bring the catheter back to the original shape. The repulsive force thus generated is so large that the distal end 138a of the catheter is moved toward the entrance of the left coronary artery so as to be inserted into the left coronary artery easily, promptly and with safety without requiring an operation to impart a torque.

It is desirable for a curvature radius R1 of the first curved portion 131 to fall within a range of between about 30 mm and about 100 mm under a free state free from an external force.

The first substantially straight portion 132 contiguous to the first curved portion 131 is substantially straight under a free state free from an external force. It is desirable for the first substantially straight portion 132 to have a length L1 falling within a range of between about 30 mm and about 80 mm.

The second curved portion 133 contiguous to the first substantially straight portion 132 is bent under a free state free from an external force in a direction opposite to the bending direction of the first curved portion 131, i.e., bent in the counterclockwise direction in FIG. 1. It is desirable for an angle α2 made in the second curved portion 133 between the first straight portion 132 and the second straight portion 134 to fall within a range of between about 30° and about 150° under a free state free from an external force, preferably between about 50° and about 100°. Also, it is desirable for a curvature radius R2 of the second curved portion 133 to be about 5 to 20 mm under a free state free from an external force.

The second substantially straight portion 134 is substantially straight under a free state free from an external force. When the catheter 10 of the present invention is retained in the heart of the patient, the second substantially straight portion 134 is in contact with substantially the entire length of the wall of the aortic arch on the side opposite to the entrance of the left coronary artery. As a result, the distal end 138a of the catheter is not deviated from the entrance of the left coronary artery so as to impart a sufficient back-up force to the catheter. When the catheter of the present invention is used as a guiding catheter together with a treating catheter into which the guiding catheter is inserted, the second substantially straight portion 134 permits assisting without fail the operation of the treating catheter. It is desirable for the second substantially straight portion 134 to have a length of about 10 mm to about 50 mm.

The third curved portion 135 contiguous to the second substantially straight portion 134 is bent under a free state free from an external force in the bending direction of the second curved portion 133, i.e., in the counterclockwise direction in FIG. 1. It is desirable for an angle α3 made in the third curved portion 135 between the second substantially straight portion 134 and the third substantially straight portion 136 to fall within a range of between about 30° and about 150°, preferably between about 60° and about 120°, under a free state free from an external force. Also, it is desirable for the third curved portion 135 to have a curvature radius R3 of about 5 mm to about 20 mm under a free state free from an external force.

The third substantially straight portion 136 contiguous to the third curved portion 135 is substantially straight under a free state free from an external force. When the catheter of the present invention is retained in the heart of the patient, the length L3 of the third substantially straight portion 136 is substantially equal to the length between the wall of the aortic arch on the side opposite to the entrance of the left coronary artery and the left coronary artery. To be more specific, the length L3 should be about 10 mm to about 100 mm, preferably 30 mm to 50 mm.

The fourth curved portion 137 contiguous to the third substantially straight portion 136 is bent under a free state free from an external force in the bending direction of the third curved portion 135, i.e., in the counterclockwise direction in FIG. 1. It is desirable for an angle α4 made in the fourth curved portion 137 between the third substantially straight portion 136 and the distal end portion 138 to fall within a range of between about 30° and about 150°, preferably between about 60° and about 130°, under a free state free from an external force. Also, it is desirable for the fourth curved portion 137 to have a curvature radius R4 of about 5 mm to about 20 mm under a free state free from an external force.

The distal end portion 138 is substantially straight under a free state free from an external force. It suffices for the distal end portion 138 to have a length L4 which prevents the distal end portion 138 from entering unduly deep into the left coronary artery and permits the distal end portion 138 to be inserted into and retained in the left coronary artery without fail. To be more specific, it is desirable for the length L4 to fall within a range of between about 5 mm and about 50 mm.

In the present invention, the entire region of the catheter body 11 should desirably be formed of a laminate structure consisting of a plurality of layers. For example, the catheter body 11 should preferably be of a three-layer structure consisting of an inner layer 21, an intermediate layer 22 and an outer layer 23, as shown in FIG. 2. As apparent from FIG. 2, a lumen 25 is formed along the axis of the catheter body 11 in a manner to extend over the entire region of the catheter body 11. In general, the lumen 25 has a diameter of 0.7 mm to 2.3 mm.

Each of these inner layer 21, intermediate layer 22 and outer layer 23 can be formed of, for example, a polyamide resin, e.g., nylon 11, nylon 12, or nylon 6, a polyesterpolyamide resin, e.g., GRYLAX (trade name) available from DIC, a polyetherpolyamide resin, e.g., PEBAX (trade name) available from Atochem Inc., a polyurethane, ABS resin, or a fluorine-containing resin, e.g., PFA, PTFA, ETFE. Particularly, it is desirable to use a fluorine-containing resin, preferably PTFE, an ABS resin or nylon 12 for forming the inner layer 21. Where the inner layer 21 is formed of a fluorine-containing resin, it is possible to improve the operability of the guide wire inserted into the lumen 25 and a treating catheter. Also, where the inner layer 21 is formed of an ABS resin or nylon 12, an appropriate mechanical strength can be imparted to the distal segment 13 having curved portions of the catheter body 11.

It should be noted that the catheter body 11 is inserted into a blood vessel while observing the position of the catheter body 11 by radioscopy. Therefore, it is desirable to mix in advance a radiopaque material such as barium sulfate, bismuth oxide or tungsten with the material of the catheter body 11, e.g., inner layer 21, intermediate layer 22 and/or outer layer 23. The thickness of each of the layers 21 to 23 is not particularly limited in the present invention, though the inner layer 21 is formed thinner in the example shown in FIG. 2, compared with each of the intermediate layer 22 and the outer layer 23. These layers 21 to 23 are bonded to each other with a suitable adhesive or thermally fused together. Alternatively, these layers 21 to 23 are formed integral by a clad molding.

In the present invention, it is desirable to embed a reinforcing material within the catheter body 11 over the entire region except a distal end section covering a predetermined length from the distal end 138a. Preferably, a metal mesh 24 should be embedded as a reinforcing material in the intermediate layer 22, as shown in FIG. 2. The metal mesh 24 (reinforcing material) prevents the catheter body 11 from being bent and, when the catheter body 11 is required to be rotated, permits improving the torque. It is desirable for the metal mesh 24 to be embedded over the substantially entire length of the catheter body 11 except a distal end section covering a predetermined length from the distal end 138a. Where the metal mesh 24 does not extend to cover the distal end section noted above, the distal end 138a of the catheter is prevented from doing damage to the wall of the blood vessel. Also, the catheter is prevented from becoming unduly rigid and, thus, from entering the left ventricle rather than the entrance of the coronary artery. The length of the distal end section in which the metal mesh 24 is not embedded should be determined appropriately in view of the material of the catheter body 11 and the difference between the inner and outer diameters of the catheter body 11, i.e., the total thickness of the inner layer 21, intermediate layer 22 and outer layer 23. For example, where the difference between the inner and outer diameters of the catheter body 11 is large, or where the catheter body 11 is formed of a material having a high elasticity, it is desirable for the metal mesh-free distal end section to be set longer.

In general, the distal end of the metal mesh 24 should be positioned 5 to 150 mm, preferably 5 to 100 mm, apart from the distal end 138a of the catheter body 11. Where the metal mesh 24 is not present in a region exceeding 150 mm from the distal end 138a of the catheter body 11, the torque fails to be transmitted sufficiently to the distal end 138a in some cases. The metal mesh 24 can be formed of thin wires of, for example, stainless steel, tungsten, nickel-titanium alloy or carbon fiber. The diameter of the component wire should be, for example, about 0.01 to 0.2 mm.

The lumen 25 extending along the axis of the catheter body 11 is open at the distal end 138a of the catheter body 11. When the catheter is introduced into an aimed site, a treating catheter is inserted into the lumen 25. Also, for an angiography procedure, a contrast medium is supplied into the lumen 25 so as to be injected through the open distal end of the lumen 25 into an aimed site. Incidentally, at least one side hole (not shown) communicating with the lumen 25 through the wall of the catheter body 11 may be formed so as to permit the contrast medium to be injected into the aimed site through the side hole as well as through the open distal end of the lumen 25.

FIGS. 3 to 5 collectively show how to use the catheter of the present invention when the catheter is used as a guiding catheter for a treating catheter.

As shown in FIG. 3, a catheter introducer 31 is stuck at the brachial artery (or radial artery) 35 by the Seldinger technique. Then, the catheter 10 of the present invention having a guide wire 34 inserted into the lumen is inserted into a sheath 32 of the catheter introducer 31. Further, the guide wire 34 is moved forward first to permit the distal end portion 138 of the catheter body 11 to be inserted through the open distal end of the sheath 32 into the brachial artery or radial artery 35. In this step, the insertion of the guide wire 34 causes the catheter body 11 to be stretched substantially straight including the distal segment. Also, the catheter body 11 is moved within the artery while changing its shape in accordance with the change in the shape of the guide wire 34.

In the next step, the catheter 10 and the guide wire 34 are gradually moved in a direction denoted by an arrow in FIG. 3 so as to be inserted through the brachiocephalic trunk into the aorta ascendens. In this step, the distal end portion 138 of the catheter body 11 passes through bent portions of the blood vessel. Therefore, various operations including the moving forward/backward of the guide wire 34 and the moving forward/backward and rotation of the catheter 10 are carried out in an appropriate combination so as to permit the catheter 10 to be moved within the blood vessel.

As shown in FIG. 4, the catheter 10 introduced through the brachiocephalic trunk 41 into the aorta ascendens 42 proceeds toward the left ventricle 46. If the catheter 10 is further moved forward, the distal end portion of the guide wire 34 abuts against the Valsalva cave 45. If the guide wire 34 is withdrawn in this step from the catheter 10, the distal segment of the catheter body 11 is brought back to its original curved shape so as to generate a repulsive force. Because of the repulsive force, the distal end portion 138 of the catheter is positioned to face the entrance of the left coronary artery 43 so as to be inserted thereinto. If the distal end portion 138 of the catheter is not inserted into the left coronary artery 43, the distal end portion 138 can be inserted easily into the left coronary artery 43 by lightly rotating the proximal end portion of the catheter 10 in the counterclockwise direction.

Under the condition described above, the second substantially straight portion 134 included in the distal segment 13 of the catheter body is in contact with the wall 47 of the aortic arch positioned on the side opposite to the entrance of the left coronary artery 43. Because of the particular shape of the distal segment 13, a large back-up force is generated in the catheter 10. Also, the catheter is held stationary satisfactorily, with the result that the distal end portion 138 of the catheter body is unlikely to be deviated from the entrance of the left coronary artery 43. To be more specific, the second substantially straight portion 134 abuts against the wall 47 of the aortic arch, as described above. Therefore, even if a push-back force is generated to push back the catheter body 11 from the entrance of the left coronary artery 43, a back-up force coping with the push-back force is imparted to the catheter body 11 so as to retain the catheter body in the position shown in FIG. 5. It follows that the distal end portion 138 is not deviated from the entrance of the left coronary artery 43. In this step, the first curved portion 131 included in the distal segment of the catheter body 11 is positioned in a region including the outlet portion of the brachiocephalic trunk 41 and the aortic arch 48, as shown in FIG. 5.

After the distal end portion 138 of the catheter is inserted into the left coronary artery 43 in the way mentioned above, a connector (not shown) is connected to a Y-connector 33, shown in FIG. 3, mounted at the proximal end of a catheter hub 31 for injection of a contrast medium. The injected contrast medium passes through the lumen of the catheter body 11 so as to be ejected through the open distal end of the lumen into the desired site of the left coronary artery. As a result, the inserted position of the catheter within the left coronary artery can be confirmed. It is also possible to perform angiography. Incidentally, a reference numeral 44 in each of FIGS. 4 and 5 represents the right coronary artery.

Then, a treating catheter (not shown) such as a balloon-tip catheter for PTCA is inserted from the proximal end of the Y-connector 33 into the aimed site through the lumen of the catheter body. In general, the catheter body of a treating catheter has a rigidity. Therefore, when the treating catheter is operated, the reaction force causes in many cases the guiding catheter to be pushed back from the desired retention site of the left coronary artery. In the event of this situation, it is difficult to insert the treating catheter into the aimed site. It follows that the back-up force of the guiding catheter is very important. On the other hand, the shape of the catheter is defined in the present invention as described previously. To reiterate, the distal segment of the catheter body is shaped such that the second substantially straight portion included in the distal segment abuts against the wall 47 of the aortic arch, making it possible to introduce the catheter into the entrance of the left coronary artery easily, with safety and promptly without requiring troublesome operations and without imparting a high torque transmitting capability to the catheter.

EXAMPLE

A catheter constructed as shown in FIG. 1 and specified as given below was prepared and used for clinical diagnosis:

Entire length of catheter body 11: 100 cm;

Outer diameter of catheter body 11: 2.0 mm;

Inner diameter (lumen diameter) of catheter body 11: 1.60 mm;

Construction of catheter body 11: laminate structure consisting of inner layer 21 made of a fluorine-containing resin, intermediate layer 22 made of ABS-mixed polyurethane, and outer layer 23 made of polyurethane;

Length of distal segment 13 when stretched straight: 40 cm;

Angle $\alpha_1$ made between proximal segment 12 and first straight portion 132: 115°;

Angle $\alpha_2$ made between first straight portion 132 and second straight portion 134: 120°;

Angle $\alpha_3$ made between second straight portion 134 and third straight portion 136: 90°;

Angle $\alpha_4$ made between third straight portion 136 and distal end portion 138: 110°;

Curvature radius R1 of first curved portion 131: 60 mm;

Curvature radius R2 of second curved portion 133: 18 mm;

Curvature radius R3 of third curved portion 135: 11 mm;
Curvature radius R4 of fourth curved portion 137: 14 mm;
Length of first straight portion 132: 53 mm;
Length of second straight portion 134: 20 mm;
Length of third straight portion 136: 20 mm;
Length of distal end portion 138: 10 mm;

Reinforcing material (metal mesh) 24: A metal mesh prepared by braiding a stainless steel wire having a diameter of 50 μm was embedded in the boundary region between the inner layer 21 and the intermediate layer 22 over the entire length of the catheter body 11 except 20 mm of the distal end section from the distal end 138a.

A 6F sheath (F=about ⅓ mm) was percutaneously retained at the brachial artery for each of five male patients aged 55 to 65 and two female patients aged 60 and 70. Then, the catheter specified above was inserted through the sheath into the left coronary artery of each patient so as to perform coronary arteriography. The catheter was smoothly inserted into the left coronary artery for each of the patients. Also, the catheter was found to assist efficiently the operation of a treating catheter. Withdrawal, vibration, etc. of the catheter were not caused by the injection of a contrast medium and the reaction accompanying the operation of the treating catheter, with the result that the manual operation was finished easily and with safety for all the patients. Further, any patient need not keep absolutely quiet after completion of the manual operation. All the patients stated that they were highly comfortable after the manual operation. Still further, a complication such as bleeding was not found at all.

As described above, the catheter of the present invention can be percutaneously introduced through the artery in the arm such as the brachial artery or radial artery into the left coronary artery easily, with safety and promptly, though it was difficult in the past to introduce the catheter through the artery in the arm. It follows that the catheter of the present invention makes it possible to form an image of the left coronary artery and to introduce and assist a treating catheter with safety and without fail. In addition, the care after the operation is rendered easy, and the burden given to the patient by the manual operation can be markedly lessened. Still further, the possibility of occurrence of a complication accompanying the use of a urinary tract catheter can be avoided in the case of using the catheter of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. A catheter whose distal end can be introduced through an artery in the arm into the entrance of the left coronary artery, comprising a catheter body having an outer diameter of at most 2.7 mm throughout its entire length and having a proximal segment substantially straight under a free state and a distal segment having a curved shape under a free state,
    said distal segment including:
        a first substantially straight portion contiguous to said proximal segment through a first curved portion,
        a second substantially straight portion contiguous to said first substantially straight portion through a second curved portion bent in a direction opposite to the bending direction of the first curved portion,
        a third substantially straight portion contiguous to said second substantially straight portion through a third curved portion bent in the bending direction of said second curved portion, and
        a substantially straight distal end portion including said distal end and contiguous to said third substantially straight portion through a fourth curved portion bent in the bending direction of said third curved portion, a first imaginary straight extension line extending from the distal end of said proximal segment of the catheter body toward the distal end side of the catheter crossing a second imaginary straight extension line extending from the proximal end of said first substantially straight portion of the distal segment toward the proximal side of the catheter.

2. The catheter according to claim 1, wherein an angle made between said proximal segment and said first substantially straight portion falls within a range of between 90° and 150°.

3. The catheter according to claim 2, wherein an angle made between the first substantially straight portion and said second substantially straight portion falls within a range of between 30° and 150°.

4. The catheter according to claim 3, wherein an angle made between the second substantially straight portion and said third substantially straight portion falls within a range of between 30° and 150°.

5. The catheter according to claim 4, wherein an angle made between the third substantially straight portion and said distal end portion falls within a range of between 30° and 150°.

6. The catheter according to claim 5, wherein said first curved portion has a curvature radius falling within a range of between 30 mm and 100 mm.

7. The catheter according to claim 6, wherein said second curved portion has a curvature radius falling within a range of between 5 mm and 20 mm.

8. The catheter according to claim 7, wherein said third curved portion has a curvature radius falling within a range of between 5 mm and 20 mm.

9. The catheter according to claim 8, wherein said fourth curved portion has a curvature radius falling within a range of between 5 mm and 20 mm.

10. The catheter according to claim 9, wherein said first substantially straight portion has a length falling within a range of between 30 mm and 80 mm.

11. The catheter according to claim 10, wherein said second substantially straight portion has a length falling within a range of between 10 mm and 50 mm.

12. The catheter according to claim 11, wherein said third substantially straight portion has a length falling within a range of between 10 mm and 100 mm.

13. The catheter according to claim 12, wherein said distal end portion has a length falling within a range of between 5 mm and 50 mm.

14. The catheter according to claim 1, wherein said catheter body is shaped to permit said second substantially straight portion to be in contact with the wall of the aortic arch on the side opposite to the entrance of the left coronary artery.

15. The catheter according to claim 1, wherein said catheter body is shaped such that, when the distal end of the catheter body is positioned at the entrance of the left coronary artery, said first curved portion is positioned to extend from the brachiocephalic trunk into the aortic arch.

16. The catheter according to claim 1, wherein a reinforcing member is embedded within the catheter body over the entire length except the distal end section which is 5 to 150 mm long as measured from the distal end.

17. The catheter according to claim 16, wherein said reinforcing member comprises a metal mesh.

18. The catheter according to claim 1, wherein said catheter body is of laminate structure comprising a plurality of layers.

19. A catheter whose distal end can be introduced through an artery in the arm into the entrance of the left coronary artery, comprising a catheter body having a proximal segment substantially straight under a free state and a distal segment having a curved shape under a free state, said distal segment including:
- a first substantially straight portion contiguous to said proximal segment through a first curved portion,
- a second substantially straight portion contiguous to said first substantially straight portion through a second curved portion bent in a direction opposite to the bending direction of the first curved portion,
- a third substantially straight portion contiguous to said second substantially straight portion through a third curved portion bent in the bending direction of said second curved portion, and
- a substantially straight distal end portion including said distal end and contiguous to said third substantially straight portion through a fourth curved portion bent in the bending direction of said third curved portion,
- a first imaginary straight extension line extending from the distal end of said proximal segment of the catheter body toward the distal end side of the catheter crossing a second imaginary straight extension line extending from the proximal end of said first substantially straight portion of the distal segment toward the proximal side of the catheter.

20. The catheter according to claim 19, wherein an angle between said proximal segment and said first substantially straight portion falls within a range of between 90° and 150°.

* * * * *